United States Patent
Han et al.

(10) Patent No.: US 12,019,094 B2
(45) Date of Patent: Jun. 25, 2024

(54) DEVICE FOR MEASURING MICROFLUID FLOW VELOCITY BY USING ULTRA THIN FILM, HAVING SEPARABLE STRUCTURE

(71) Applicant: INJE UNIVERSITY INDUSTRY-ACADEMIC COOPERATION FOUNDATION, Gimhae-si (KR)

(72) Inventors: Ki-Ho Han, Busan (KR); Jin-Ho Kim, Busan (KR)

(73) Assignee: INJE UNIVERSITY INDUSTRY-ACADEMIC COOPERATION FOUNDATION, Gimhae-si (KR)

( * ) Notice: Subject to any disclaimer, the term of this patent is extended or adjusted under 35 U.S.C. 154(b) by 1097 days.

(21) Appl. No.: 16/603,013

(22) PCT Filed: Aug. 21, 2017

(86) PCT No.: PCT/KR2017/009069
§ 371 (c)(1),
(2) Date: Oct. 4, 2019

(87) PCT Pub. No.: WO2018/186539
PCT Pub. Date: Oct. 11, 2018

(65) Prior Publication Data
US 2020/0033376 A1 Jan. 30, 2020

(30) Foreign Application Priority Data
Apr. 6, 2017 (KR) .......................... 10-2017-0044621

(51) Int. Cl.
*G01P 5/12* (2006.01)
*B01L 3/00* (2006.01)

(52) U.S. Cl.
CPC .......... *G01P 5/12* (2013.01); *B01L 3/502715* (2013.01); *B01L 2200/0689* (2013.01);
(Continued)

(58) Field of Classification Search
CPC .............. B01J 19/24; B01L 2200/0689; B01L 2300/0645; B01L 2300/0663;
(Continued)

(56) References Cited

U.S. PATENT DOCUMENTS

| 5,463,906 A | 11/1995 | Spani et al. |
| 2008/0280112 A1* | 11/2008 | Langereis ........... B81C 1/00119 428/201 |

(Continued)

FOREIGN PATENT DOCUMENTS

| JP | 2002-122454 A | 4/2002 |
| JP | 2002-340646 A | 11/2002 |
| JP | 2006-250955 A | 9/2006 |
| JP | 2007-212199 A | 8/2007 |

OTHER PUBLICATIONS

International Search Report for PCT/KR2017/009069 dated Jan. 5, 2018 [PCT/ISA/210].

*Primary Examiner* — Gurpreet Kaur
(74) *Attorney, Agent, or Firm* — Sughrue Mion, PLLC (57) ABSTRACT

Provided is a device for measuring a microfluid flow velocity, having a structure separable by an ultra-thin film, the device including a first panel including a flow velocity measurement structure configured to measure a flow velocity of a fluid, a second panel configured to be separated from the first panel and including a microfluid channel through which a sample passes, and the ultra-thin film formed in a portion where the first panel and the second panel adjoin each other, the ultra-thin film being configured to separate the first panel and the second panel so that the sample passing through the microfluid channel does not come into (Continued)

direct contact with the flow velocity measurement structure, in which the first panel including the flow velocity measurement structure is usable multiple times repeatedly.

10 Claims, 10 Drawing Sheets

(52) U.S. Cl.
CPC .................. *B01L 2300/0627* (2013.01); *B01L 2300/0645* (2013.01); *B01L 2300/0663* (2013.01); *B01L 2300/12* (2013.01); *B01L 2300/14* (2013.01); *B01L 2300/1805* (2013.01)

(58) Field of Classification Search
CPC ..... B01L 2300/0816; B01L 2300/0887; B01L 2300/12; B01L 2300/14; B01L 2300/1805; B01L 2300/1827; B01L 2300/0627; B01L 3/502707; B01L 3/502715; C12M 1/38; C12N 15/8218; C12N 15/8261; C12N 15/8273; G01F 1/6845; G01F 1/6847; G01K 13/02; G01N 35/08; G01P 5/12

See application file for complete search history.

(56) References Cited

U.S. PATENT DOCUMENTS

| | | | |
|---|---|---|---|
| 2009/0032401 A1* | 2/2009 | Ronaghi | B01L 3/502761 204/647 |
| 2009/0066339 A1* | 3/2009 | Glezer | B01L 3/502715 250/493.1 |
| 2011/0111517 A1* | 5/2011 | Siegel | B01L 3/502707 436/164 |
| 2012/0006681 A1* | 1/2012 | Kaler | B01F 33/3031 204/453 |
| 2015/0316454 A1* | 11/2015 | Wimberger-Friedl | B01L 3/502715 435/309.1 |

* cited by examiner

DEVICE FOR MEASURING MICROFLUID FLOW VELOCITY BY USING ULTRA THIN FILM, HAVING SEPARABLE STRUCTURE

CROSS REFERENCE TO RELATED APPLICATIONS

This application is a National Stage of International Application No. PCT/KR2017/009069, filed on Aug. 21, 2017, which claims priority from Korean Patent Application No. 10-2017-0044621, filed on Apr. 6, 2017, the entire disclosures of which are incorporated herein by reference.

TECHNICAL FIELD

The present invention relates to a device for measuring a microfluid flow velocity having a structure separable by an ultra-thin film, and more particularly, to a device for measuring a microfluid flow velocity, in which a panel including a channel through which a sample flows and a panel including a flow velocity measurement structure are separable by an ultra-thin film, such that the device is easily manufactured by having a simple structure, manufacturing costs thereof are lower than those of a device for measuring a flow velocity of a fluid in the related art, and the panel including the flow velocity measurement structure for measuring a flow velocity may be permanently used.

BACKGROUND ART

Recently, a method of measuring a flow velocity of a fluid in a microfluid structure typically uses a structure in which measurement sensors are positioned at both ends thereof and a heater is positioned between the measurement sensors. The measurement principle will be described. The fluid on the heater is higher than the ambient fluid temperature. If no fluid flows, the temperatures of the fluids in two measuring channels at both sides of the heater are equal to each other. In contrast, if the fluid flows through the channels, there is a difference between a temperature measured by the measurement sensor at a rear side of the heater and a temperature measured by the measurement sensor at a front side of the heater. A resistance difference between the two measurement sensors occurs by the temperature difference, and a flow velocity of the fluid is measured by electrically measuring the resistance difference.

In the related art, a general device for measuring a flow velocity of a fluid has an integrated structure in which a channel for a fluid, a heater, and a measurement sensor are manufactured in one structure. For this reason, the device for measuring a flow velocity of a fluid is generally difficult to manufacture and expensive, and in particular, in the case of using a biological sample, the device cannot be reused, so that the device needs to be discarded after being used once, which causes a problem of a large amount of waste in terms of costs. There is a problem in that because the device for measuring a microfluid flow velocity has a price of about 3 million won, the device has a disadvantage of being too expensive to be used for single use and discarded.

In addition, in the case of the device for measuring a flow velocity of a fluid which is currently commercially available, a measurable range of the flow velocity is limited depending on a cross-sectional area of a channel through which the fluid flows, a structure of a heater, and a structure of a measurement part for measuring a flow velocity. Therefore, there is a problem in that the measurable range of the flow velocity is restricted depending on the device for measuring a flow velocity of a fluid.

DISCLOSURE

Technical Problem

The present invention has been made in an effort to solve the above-mentioned problems, and an object of the present invention is to provide a device for measuring a microfluid flow velocity, the device having a structure in which a panel including a flow velocity measurement structure and a panel including a micro-structure through which a sample passes are separated by an ultra-thin film, such that the panel including the flow velocity measurement structure may be used multiple times repeatedly.

In addition, another object of the present invention is to provide a device for measuring a microfluid flow velocity, which is easily manufactured by having a simple structure, such that manufacturing costs thereof are lower than those of a device for measuring a flow velocity of a fluid in the related art.

In addition, still another object of the present invention is to provide a device for measuring a microfluid flow velocity, in which separated panels are coupled by a vacuum coupling method that holds the separated panels by applying a vacuum between the separated panels, thereby making it possible to measure a fluid flow velocity with very excellent high-performance.

In addition, yet another object of the present invention is to provide a device for measuring a microfluid flow velocity, in which a panel including a flow velocity measurement structure and a panel including a micro-structure through which a sample passes are separable, and the panel through which the sample passes may be replaced and used in accordance with a measuring range of a fluid flow velocity intended to be measured by a user, such that the device may be used universally without limiting a measurable range of the flow velocity.

Technical Solution

In order to achieve the above-mentioned object, the present invention provides a device for measuring a microfluid flow velocity, the device including a first panel including a flow velocity measurement structure configured to measure a flow velocity of a fluid, a second panel configured to be separated from the first panel and including a microfluid channel through which a sample passes, and an ultra-thin film formed in a portion where the first panel and the second panel adjoin each other, the ultra-thin film being configured to separate the first panel and the second panel so that the sample passing through the microfluid channel does not come into direct contact with the flow velocity measurement structure, in which the first panel including the flow velocity measurement structure is usable multiple times repeatedly.

The flow velocity measurement structure may include a heater configured to apply heat to the sample passing through the microfluid channel, and two temperature measuring electrodes installed at front and rear sides of the heater to measure a resistance difference in accordance with a change in temperature of the sample when the temperature of the sample is increased by the heat generated by the heater.

In addition, the device for measuring a microfluid flow velocity according to the present invention may further include a vacuum attachment means configured to apply a vacuum to hold, by the vacuum, the first and the second panel.

Here, the vacuum attachment means may include a vacuum groove formed in surfaces of the first and second panels which adjoin each other, and a vacuum suction portion configured to communicate with the vacuum groove to apply the vacuum and hold, by the vacuum, the first panel and the second panel so that an air layer between the first panel and the second panel is completely removed.

The vacuum groove may be formed in a lower surface of the second panel, and the vacuum suction portion may be formed in an upper surface or a lateral surface of the second panel to communicate with the vacuum groove.

In addition, the vacuum groove may be formed in an upper surface of the first panel, and the vacuum suction portion may be formed in a lower surface or a lateral surface of the first panel to communicate with the vacuum groove.

In this case, the vacuum groove may be shaped and positioned to surround the microfluid channel.

Meanwhile, a material of the ultra-thin film includes one or more materials selected from polydimethyl siloxane (PDMS), polyethylene terephthalate (PET), polyimide (PI), polypropylene (PP), polymeric plastic, glass. and ceramic.

In the present invention, the microfluid channel may include a fluid injection port configured to inject the sample, a fluid channel through which the sample introduced into the fluid injection port flows, and a fluid discharge port from which the sample flowing through the fluid channel is discharged.

According to the present invention, the first panel and the second panel are separable, and the second panel including the microfluid channel through which the sample passes may be replaced and used in accordance with a measuring range of a fluid flow velocity intended to be measured by a user, such that the first panel is usable universally without limiting a measurable range of the flow velocity.

Advantageous Effects

According to the present invention described above, the device has a structure in which the panel including the flow velocity measurement structure and the panel including the micro-structure through which a sample passes are separated by the ultra-thin film, such that the panel including the flow velocity measurement structure may be used multiple times repeatedly.

In addition, the device is easily manufactured by having a simple structure, such that manufacturing costs thereof are lower than those of a device for measuring a flow velocity of a fluid in the related art, and the panel including the flow velocity measurement structure may be used almost permanently, which is very advantageous in terms of cost over the related art.

In addition, because the separated panels are coupled by the vacuum coupling method that holds the separated panels by applying a vacuum between the separated panels, it is possible to measure a fluid flow velocity with very excellent high-performance.

In addition, the panel including the flow velocity measurement structure and the panel including the micro-structure through which a sample passes are separable, and the panel through which the sample passes may be replaced and used in accordance with a measuring range of a fluid flow velocity intended to be measured by a user, such that the device may be used universally without limiting the measurable range of the flow velocity.

MODES OF THE INVENTION

Hereinafter, the present invention will be described.

The present invention provides a device for measuring a microfluid flow velocity, the device including a first panel including a flow velocity measurement structure configured to measure a flow velocity of a fluid, a second panel configured to be separated from the first panel and including a microfluid channel through which a sample passes, and an ultra-thin film formed in a portion where the first panel and the second panel adjoin each other, the ultra-thin film being configured to separate the first panel and the second panel so that the sample passing through the microfluid channel does not come into direct contact with the flow velocity measurement structure, in which the first panel including the flow velocity measurement structure is usable multiple times repeatedly.

Here, the flow velocity measurement structure may include a heater configured to apply heat to the sample passing through the microfluid channel, and two temperature measuring electrodes installed at front and rear sides of the heater to measure a resistance difference in accordance with a change in temperature of the sample when the temperature of the sample is increased by the heat generated by the heater.

In addition, the device for measuring a microfluid flow velocity according to the present invention may further include a vacuum attachment means configured to apply a vacuum to hold, by the vacuum, the first and the second panel.

Here, the vacuum attachment means may include a vacuum groove formed in surfaces of the first and second panels which adjoin each other, and a vacuum suction portion configured to communicate with the vacuum groove to apply the vacuum and hold, by the vacuum, the first panel and the second panel so that an air layer between the first panel and the second panel is completely removed.

Meanwhile, a material of the ultra-thin film includes one or more materials selected from polydimethyl siloxane (PDMS), polyethylene terephthalate (PET), polyimide (PI), polypropylene (PP), polymeric plastic, glass. and ceramic.

In the present invention, the microfluid channel may include a fluid injection port configured to inject the sample, a fluid channel through which the sample introduced into the fluid injection port flows, and a fluid discharge port from which the sample flowing through the fluid channel is discharged.

BEST MODE

Hereinafter, an exemplary embodiment of the present invention will be described in detail with reference to the accompanying drawings. However, the present invention is not limited to the exemplary embodiment disclosed herein but will be implemented in various forms. The exemplary embodiment of the present invention is provided so that the present invention is completely disclosed, and a person with ordinary skill in the art can fully understand the scope of the present invention.

Figure 1:
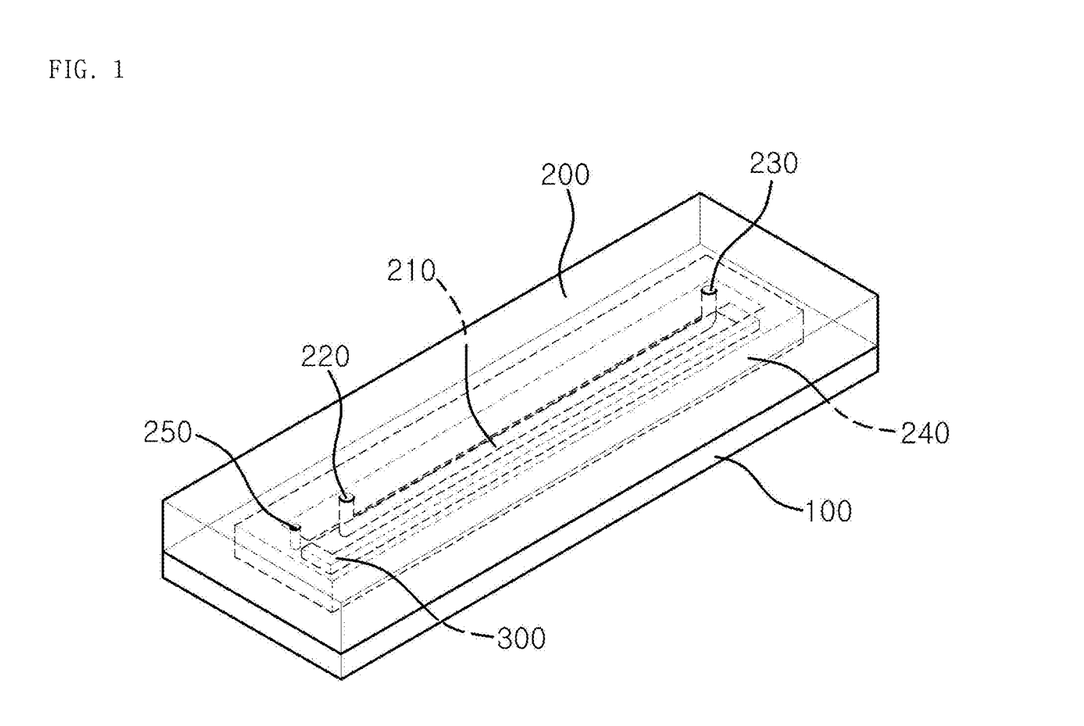
FIG. 1 is an overall perspective view illustrating a device for measuring a microfluid flow velocity according to the present invention.
Figure 2:
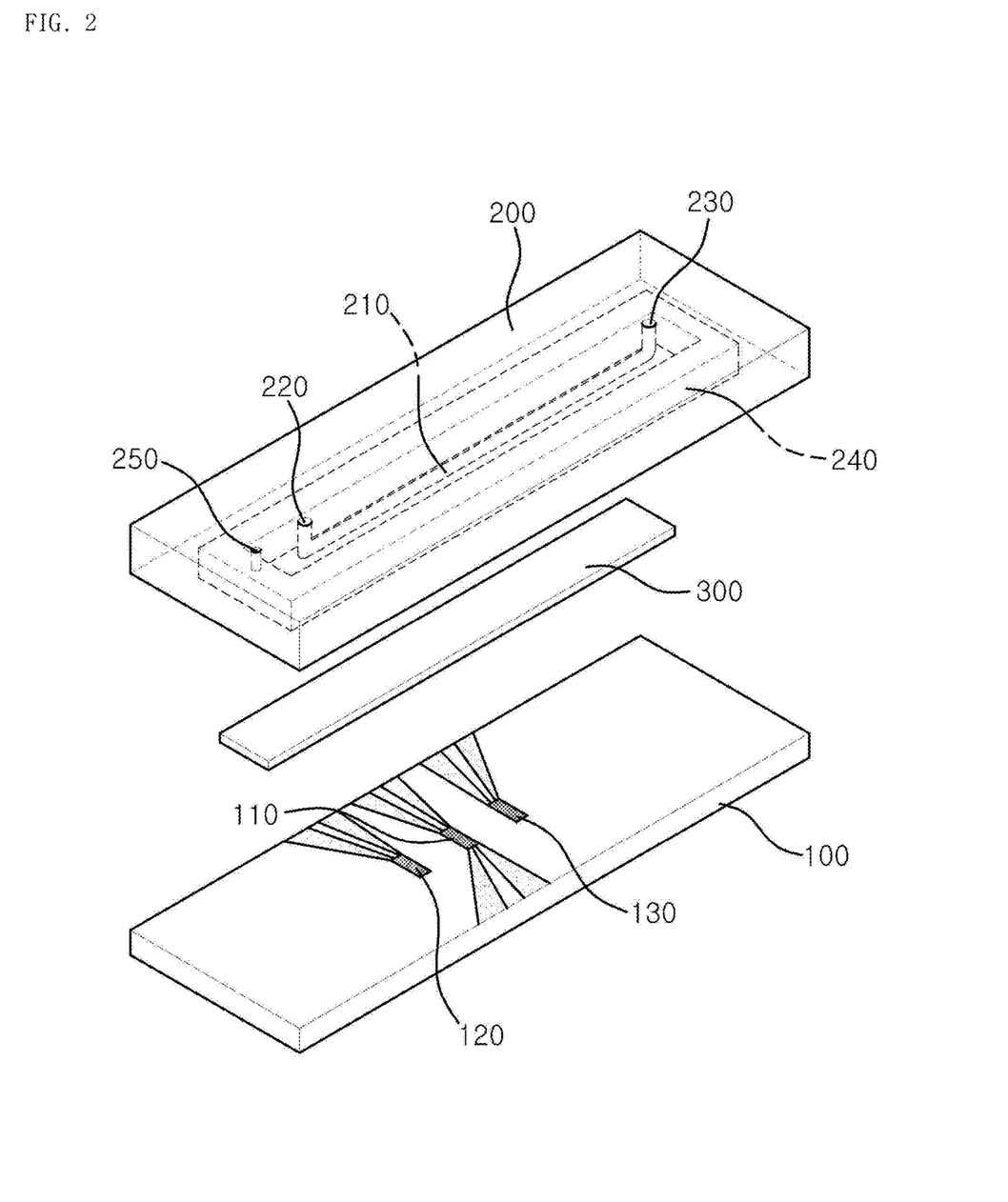
FIG. 2 is an exploded perspective view illustrating the device for measuring a microfluid flow velocity according to the present invention.
Figure 3:
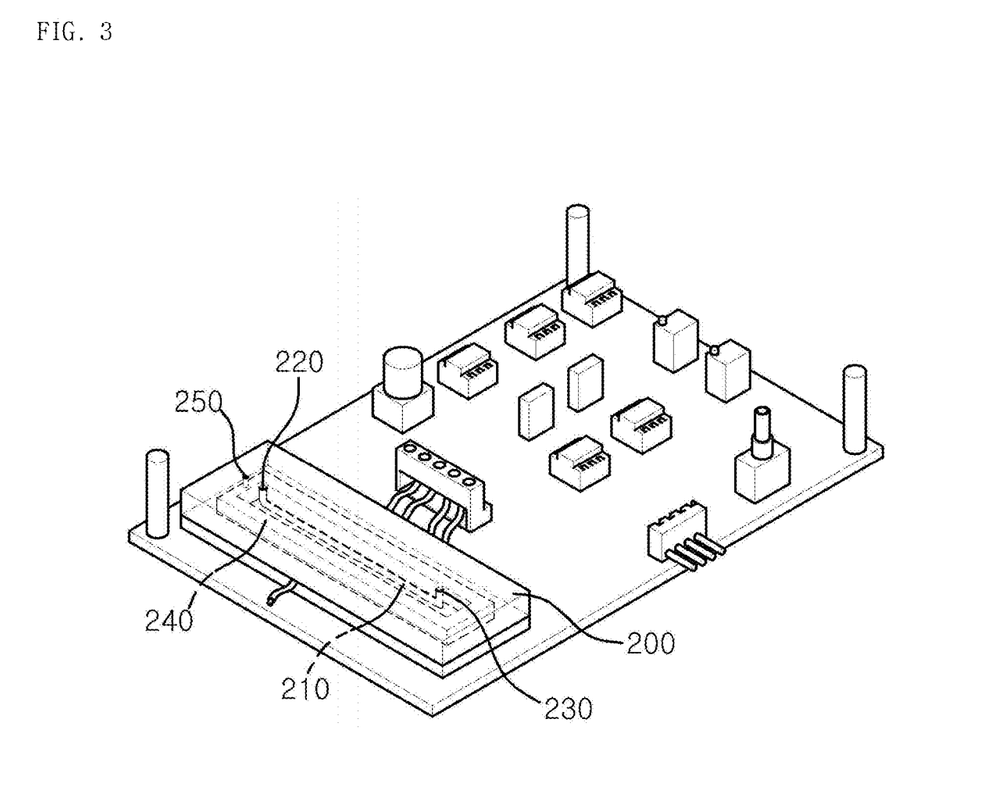
FIG. 3 is a perspective view illustrating an example in which the device for measuring a microfluid flow velocity according to the present invention is installed.

FIG. 1 is an overall perspective view illustrating a device for measuring a microfluid flow velocity according to the present invention, FIG. 2 is an exploded perspective view illustrating the device for measuring a microfluid flow velocity according to the present invention, and FIG. 3 is a perspective view illustrating an example in which the device for measuring a microfluid flow velocity according to the present invention is installed.

The device for measuring a microfluid flow velocity according to the present invention is configured such that two panels 100 and 200 are separable by using an ultra-thin film 300. The device for measuring a microfluid flow velocity includes the first panel 100 including a flow velocity measurement structure configured to measure a flow velocity of a fluid, the second panel 200 separated from the first panel 100 and including a microfluid channel through which a sample passes, and the ultra-thin film 300 formed at a portion where the first panel 100 and the second panel 200 adjoin each other, the ultra-thin film 300 being configured to separate the first panel 100 and the second panel 200 so that the sample passing through the microfluid channel does not come into direct contact with the flow velocity measurement structure.

As described above, the present invention is characterized in that the first panel 100 configured to a flow velocity of a fluid and the second panel 200 through which a sample passes are separated, and the ultra-thin film 300 is provided at the portion where the first panel 100 and the second panel 200 adjoin each other so that the sample does not come into contact with the flow velocity measurement structure.

In the related art, an integrated structure is used, in which a coating is applied onto a heater or a flow velocity measurement sensor and a heater and a measurement sensor are manufactured as one structure so that the sample does not come into direct contact with the heater. In contrast, in the case of the present invention, the two panels are separated, and the ultra-thin film 300 is applied to the separated surfaces so that the sample does not come into direct contact with the heater or the flow velocity measurement sensor, such that the first panel 100 including the flow velocity measurement structure may be permanently used.

The flow velocity measurement structure installed on the first panel 100 includes a heater 110 configured to apply heat to the sample passing through the microfluid channel, and two temperature measuring electrodes 120 and 130 installed at front and rear sides of the heater 110 to measure a resistance difference in accordance with a change in temperature of the sample when the temperature of the sample is increased by heat generated by the heater 110.

That is, a first temperature measuring electrode 120 is installed at one side of the heater 110, a second temperature measuring electrode 130 is installed at the other side of the heater 110, such that the temperature measuring electrodes are installed at the front and rear sides of the heater 110 in a direction in which the sample flows. Therefore, the resistance difference in accordance with a change in temperature of the sample is measured when a temperature of the sample passing through the microfluid channel of the second panel 200 is increased by heat generated by the heater 110.

In this case, various structures and various shapes of the heater 110 and the temperature measuring electrodes 120 and 130 may be applied to the first panel 100. The structure is limited to the structure illustrated in the drawing of the present invention as long as the structure may measure a temperature of a sample.

Meanwhile, the second panel 200 has the microfluid channel through which a sample may pass, and the microfluid channel may include a fluid injection port 220 configured to inject the sample, a fluid channel 210 through which the sample introduced into the fluid injection port 220 flows, and a fluid discharge port 230 from which the sample flow through the fluid channel 210 is discharged.

In the exemplary embodiment of the present invention, the fluid injection port 220 and the fluid discharge port 230 are formed in an upper surface of the second panel 200 so as to communicate with each other, and a lower end of the fluid injection port 220 and a lower end of the fluid discharge port 230 are connected by the fluid channel 210, such that the flow of the sample is implemented in a '⌑' shape. However, the present invention is not limited to the position where the fluid injection port 220 and the fluid discharge port 230 are formed, and in some instances, the fluid injection port 220 and the fluid discharge port 230 may be formed in a lateral surface of the second panel 200 so as to communicate with each other.

The fluid channel 210 is formed in a lower surface of the second panel 200 and allows the sample flowing through the fluid channel 210 to receive the heat from the heater 110, such that a flow velocity implemented by the heat may be measured. The ultra-thin film 300 is attached to the lower surface of the second panel 200 to prevent the sample from coming into contact with the heater 110 or the temperature measuring electrodes 120 and 130.

The ultra-thin film 300 may be formed to be thin to smoothly transfer heat, and a material of the ultra-thin film 300 one or more materials selected from polydimethyl siloxane (PDMS), polyethylene terephthalate (PET), polyimide (PI), polypropylene (PP), polymeric plastic, glass, and ceramic.

In addition, the device for measuring a microfluid flow velocity according to the present invention may further include a vacuum attachment means configured to apply a vacuum to hold, by the vacuum, the first panel 100 and the second panel 200.

Here, the vacuum attachment means may include a vacuum groove 240 formed in a surface that adjoin the first panel 100 and the second panel 200, and a vacuum suction portion 250 configured to communicate with the vacuum groove 240 and apply the vacuum.

As illustrated in FIGS. 1 and 2, the vacuum groove 240 is positioned and shaped to surround the microfluid channels 210, 220, and 230. That is, the vacuum groove 240 may be particularly formed in a quadrangular shape to include an overall region in which the fluid injection port 220, the fluid channel 210, and the fluid discharge port 230 are formed.

The vacuum suction portion 250 is connected to an external device and applies the vacuum, thereby completely removing an air layer between the first panel 100 and the second panel 200 to hold the first panel 100 and the second panel 200 by the vacuum.

Figure 4A:
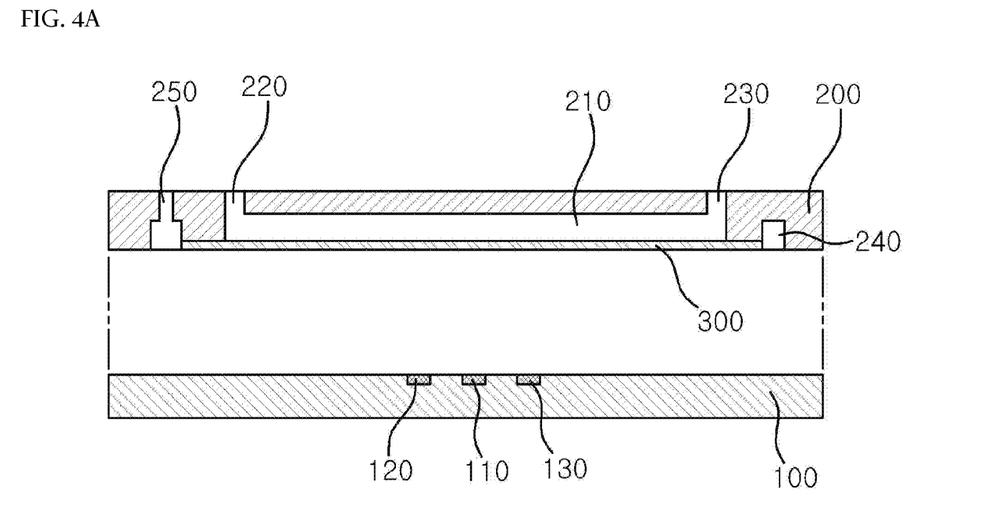
FIGS. 4A and 4B are cross-sectional views illustrating the device for measuring a microfluid flow velocity according to the present invention, that is, a cross-sectional view illustrating a first exemplary embodiment.
Figure 4B:
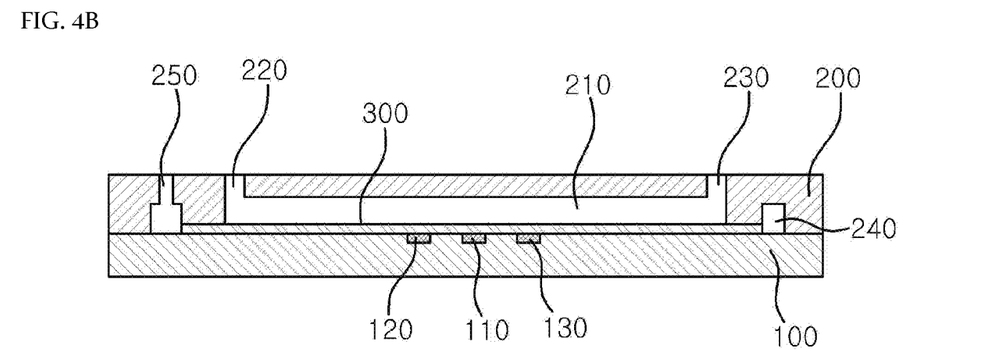

FIGS. 4A and 4B are cross-sectional views illustrating a first exemplary embodiment of the device for measuring a microfluid flow velocity according to the present invention. The vacuum groove 240 is formed in the lower surface of the second panel 200, and the vacuum suction portion 250 is formed in the upper surface of the second panel 200 to communicate with the vacuum groove 240, such that an air layer between the first panel 100 and the second panel 200 is completely removed by the vacuum suction portion 250, thereby allowing the first panel 100 and the second panel 200 to be held by the vacuum.

Figure 5A:
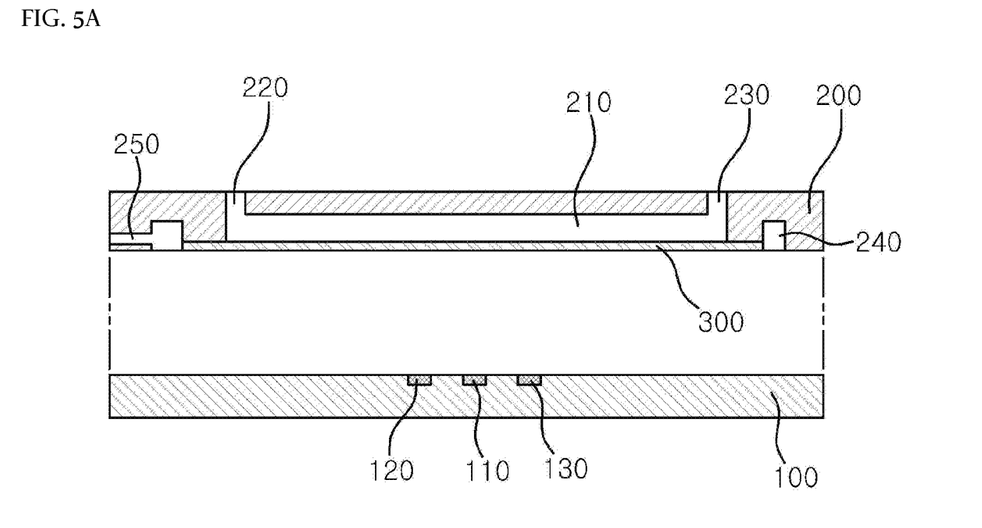
FIGS. 5A and 5B are cross-sectional views illustrating the device for measuring a microfluid flow velocity according to the present invention, that is, a cross-sectional view illustrating a second exemplary embodiment.
Figure 5B:
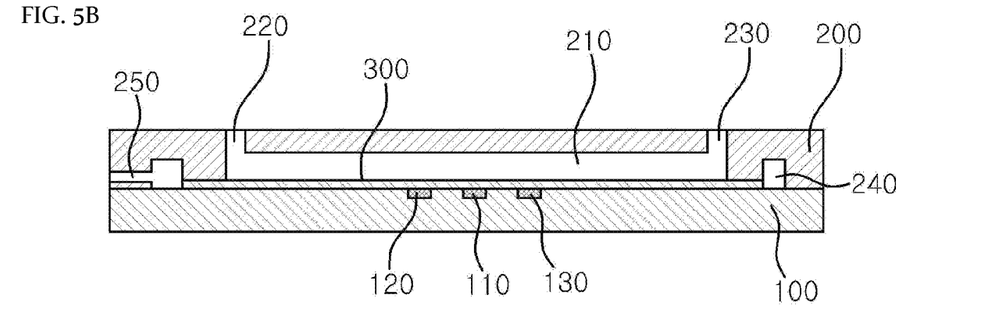

FIGS. 5A and 5B are cross-sectional views illustrating a second exemplary embodiment of the device for measuring a microfluid flow velocity according to the present invention. The vacuum groove 240 may be formed in the lower surface of the second panel 200, and the vacuum suction portion 250 may be formed in the lateral surface of the second panel 200 to communicate with the vacuum groove 240.

The vacuum groove 240 may be formed not only in the second panel 200, but also in the first panel 100.

Figure 6A:
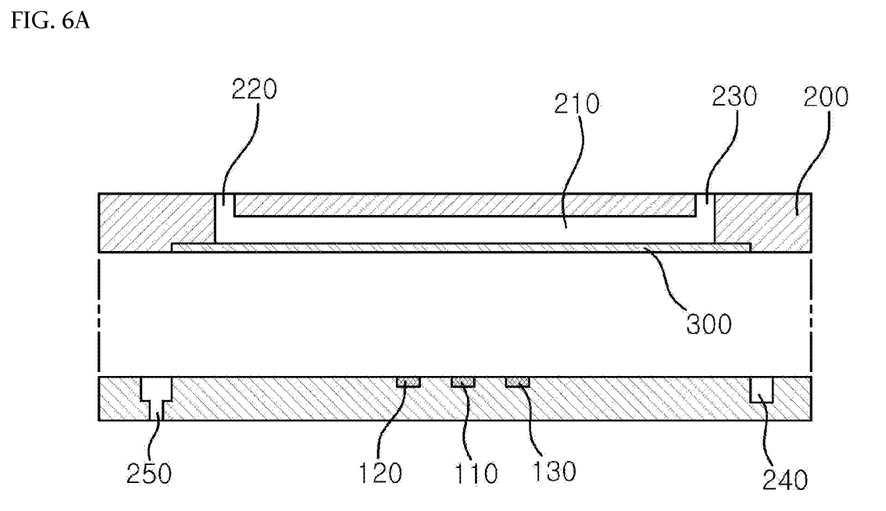
FIGS. 6A and 6B are cross-sectional views illustrating the device for measuring a microfluid flow velocity according to the present invention, that is, a cross-sectional view illustrating a third exemplary embodiment.
Figure 6B:
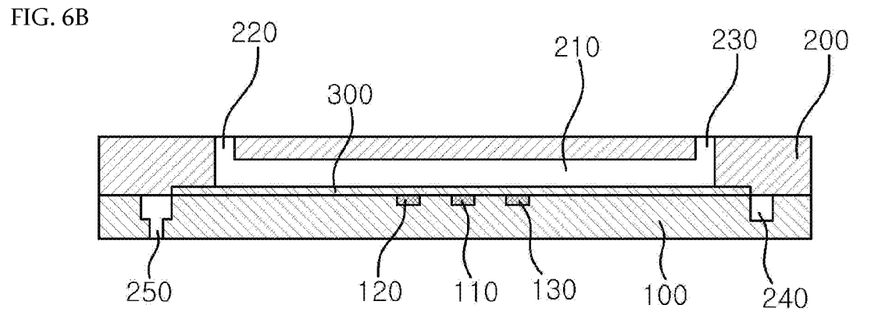

FIGS. 6A and 6B are cross-sectional views illustrating a third exemplary embodiment of the device for measuring a microfluid flow velocity according to the present invention. The vacuum groove 240 is formed in the upper surface of the first panel 100, and the vacuum suction portion 250 is formed in the lower surface of the first panel 100 to communicate with the vacuum groove 240, such that an air layer between the first panel 100 and the second panel 200 is completely removed by the vacuum suction portion 250, thereby allowing the first panel 100 and the second panel 200 to be held by the vacuum.

Figure 7A:
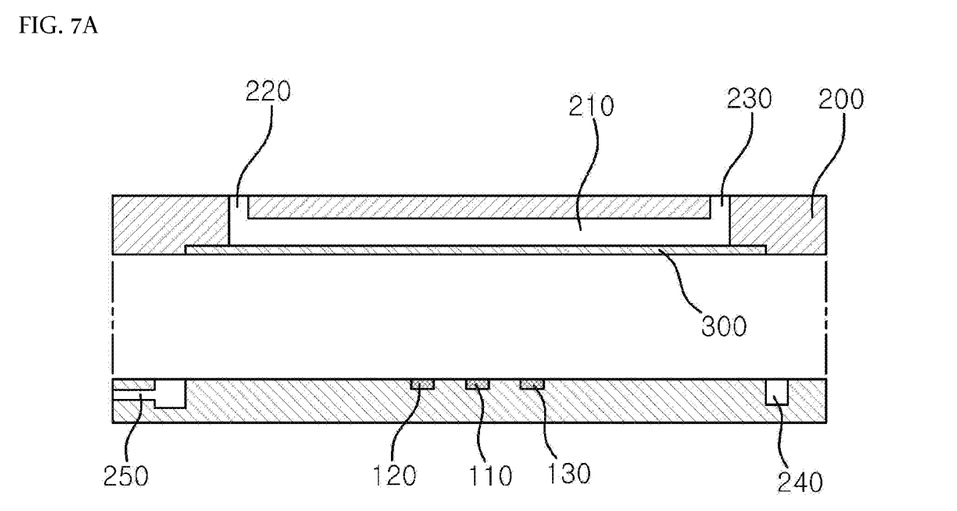
FIGS. 7A and 7B are cross-sectional views illustrating the device for measuring a microfluid flow velocity according to the present invention, that is, a cross-sectional view illustrating a fourth exemplary embodiment.
Figure 7B:
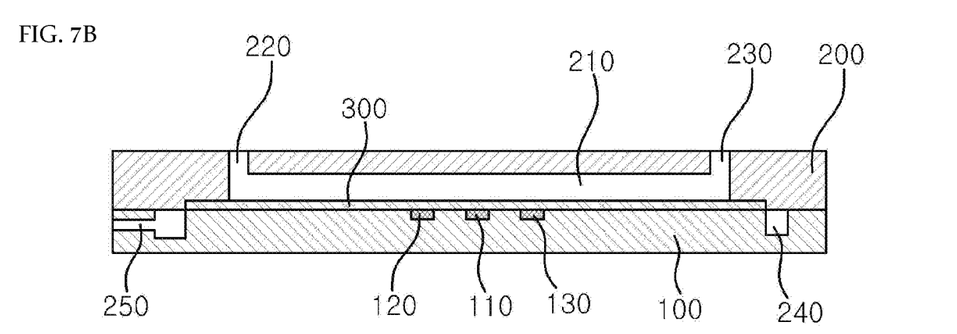

FIGS. 7A and 7B are cross-sectional views illustrating a fourth exemplary embodiment of the device for measuring a microfluid flow velocity according to the present invention. The vacuum groove 240 may be formed in the upper surface of the first panel 100, and the vacuum suction portion 250 may be formed in the lateral surface of the first panel 100 to communicate with the vacuum groove 240.

An operation and an effect of the device for measuring a microfluid flow velocity according to the present invention having the above-mentioned configurations will be described below.

As illustrated in FIG. 3, the first panel 100 having the flow velocity measurement structure is installed in a flow velocity measurement system, and the second panel 200 having the microfluid channel appropriate for the measuring range of the fluid flow velocity intended to be measured by the user, such that the flow velocity of the fluid may be measured.

As described above, according to the present invention, since the first panel 100 and the second panel 200 may be separated, the first panel 100 may be used as it is in the state of being installed in the flow velocity measurement system, and only the second panel 200 may be replaced and used in accordance with the measuring range of the fluid flow velocity intended to be measured by the user.

Therefore, the panel including the flow velocity measurement structure may be used multiple times repeatedly and almost permanently, and the second panel 200 may be easily manufactured by having a simple structure, which is very advantageous in terms of cost over the device for measuring a flow velocity of a fluid in the related art.

After the second panel 200 is attached to the first panel 100, a vacuum is applied by the vacuum suction portion 250, such that the vacuum groove 240 holds the first panel 100 and the second panel 200 by the vacuum.

Thereafter, when the heater 110 generates heat, a temperature of the sample flowing in the fluid channel 210 over the heater 110 is increased, and the temperature measuring electrode 120 provided at the front side of the heater 110 and the temperature measuring electrode 130 provided at the rear side of the heater 110 measures a resistance difference made by a change in temperature of the fluid, such that the flow velocity of the fluid may be measured.

As described above, according to the present invention, because the separated panels are coupled by the vacuum coupling method that holds the separated panels by applying a vacuum between the separated panels, it is possible to measure the fluid flow velocity with very excellent high-performance.

Meanwhile, according to the device for measuring a flow velocity according to the present invention, the second panel through which the sample passes may be replaced and used in accordance with a measuring range of a fluid flow velocity intended to be measured by a user, such that the first panel may be used universally without limiting the measurable range of the flow velocity.

Figure 8:
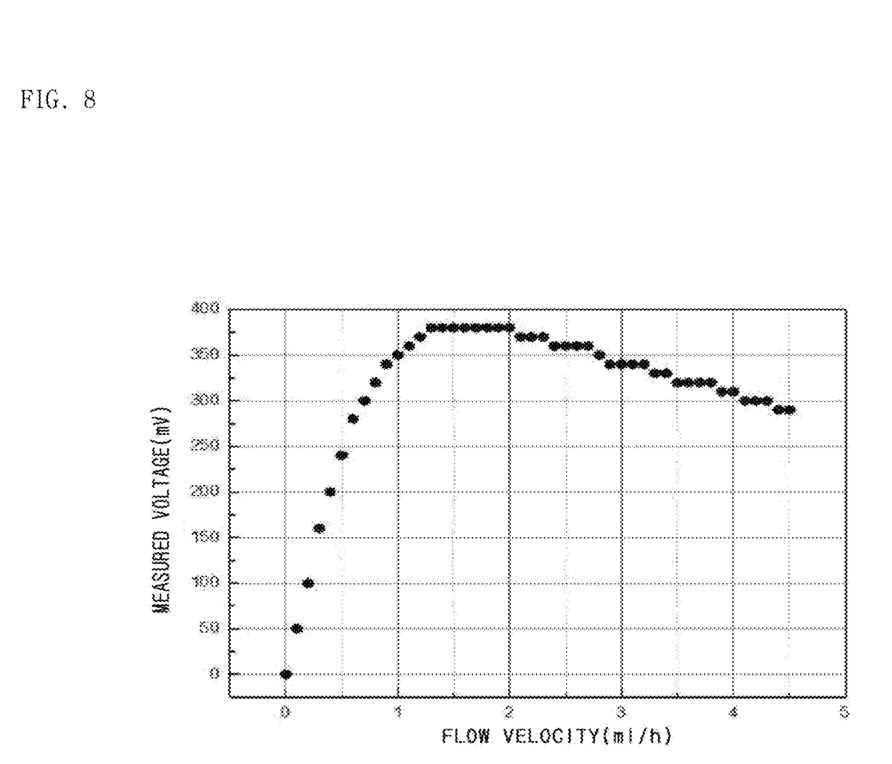
FIG. 8 is a graph illustrating an example in which a flow velocity of a fluid is measured by the device for measuring a flow velocity according to the present invention.

FIG. 8 is a graph illustrating an example in which the flow velocity of the fluid is measured by using the device for measuring a flow velocity according to the present invention. The X axis indicates the flow velocity of the fluid flowing over the heater 110 and the temperature measuring electrodes 120 and 130 of the first panel 100, and the Y axis indicates a measured voltage detected by the temperature measuring electrodes 120 and 130.

Referring to FIG. 8, the voltage value is increased from 0 ml/h to about 1.0 ml/h, but there is no great difference because the voltage value is saturated after 1.0 ml/h. Therefore, it may be determined, based on the data, that the flow velocity measured by the device for measuring a flow velocity is about 0 to 1.0 ml/h.

The product and the technology in the related art have a limitation in that the measurable range of the flow velocity is restricted. In order to overcome the limitation, the present applicant has made the present invention to provide the device for measuring a microfluid flow velocity, in which the second panel through which the sample passes may be replaced and used in accordance with the measuring range of the fluid flow velocity intended to be measured by the user, such that the first panel may be used universally without limiting the measurable range of the flow velocity.

Figure 9:
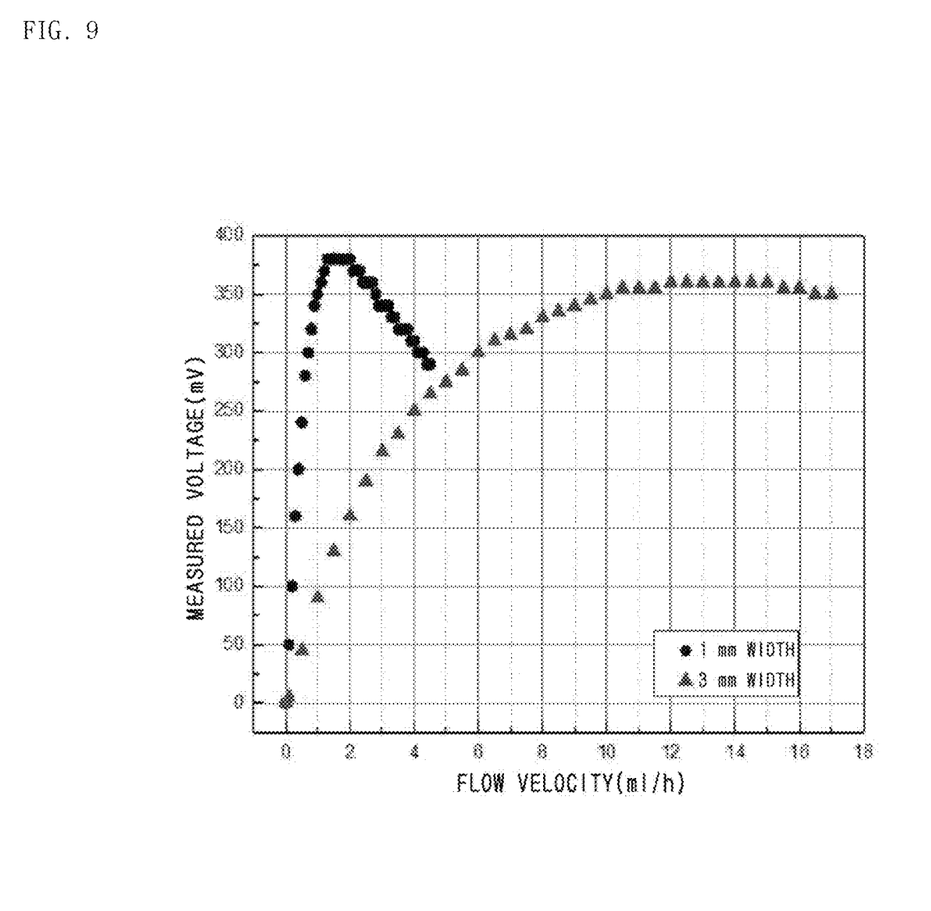
FIG. 9 is a graph illustrating an example in which a flow velocity of a fluid is measured by changing a second panel in accordance with a range for measuring a fluid.

FIG. 9 is a graph illustrating an example in which the flow velocity of the fluid while replacing the second panel in accordance with the measuring range of the fluid, and the graph in FIG. 8 is illustrated by a black circle.

Referring to the experiment in FIG. 8, a height of the fluid channel of the device for measuring a flow velocity is 50 µm, and a width of the second panel is 1 mm. As illustrated in FIG. 8, because there is a limitation in terms of the measuring range of the flow velocity, the second panel having a width of 3 mm width is manufactured, and then the measurement is performed. The measurement result is illustrated in a red triangle graph in FIG. 9.

Referring to the red graph in FIG. 9, it can be seen that unlike the data measured with the width of 1 mm, the voltage is not saturated but increases as the structure of the second panel is changed. Therefore, the second panel through which the sample passes may be replaced and used in accordance with the measuring range of the fluid flow velocity intended to be measured by the user, such that the first panel may be used universally without limiting the measurable range of the flow velocity.

Figure 10:
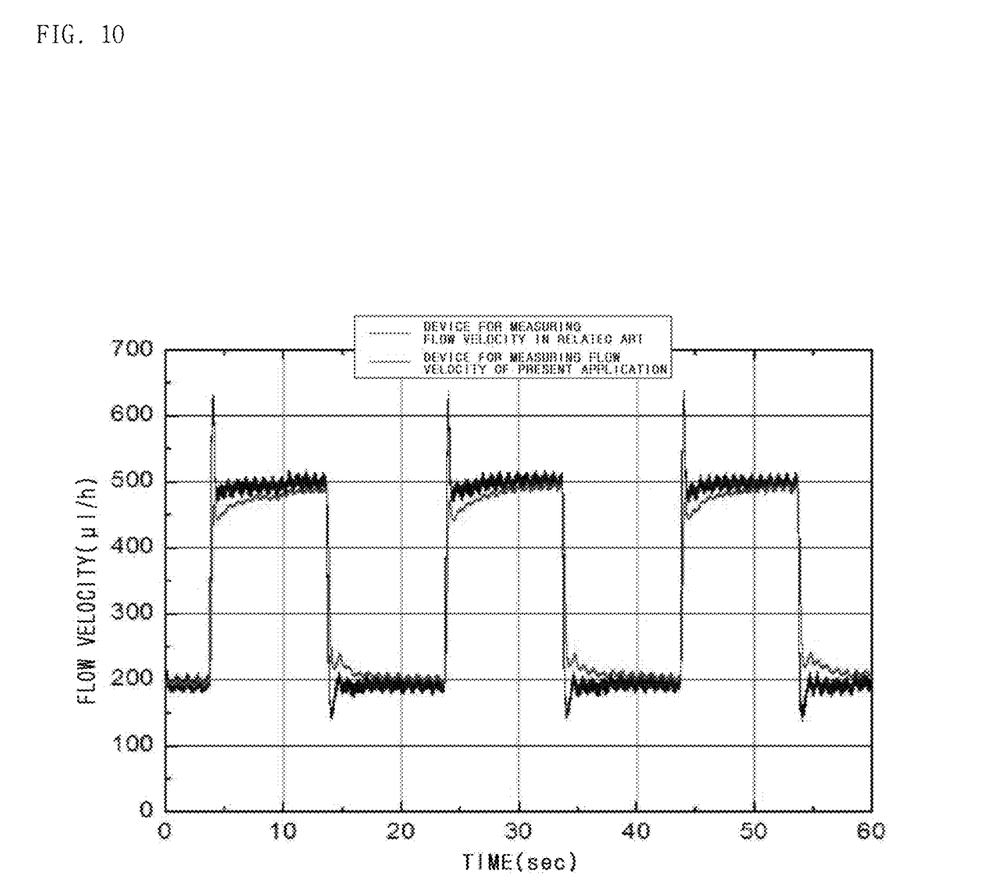
FIG. 10 is a graph illustrating values measured by comparing the device for measuring a flow velocity of the present invention with a device for measuring a flow velocity in the related art.

FIG. 10 is a graph illustrating values measured by comparing the device for measuring a flow velocity of the present invention with the device for measuring a flow velocity in the related art. A response speed and a value of the device for measuring a flow velocity according to the present invention were measured while repeatedly changing the flow velocity from 200 µl/h to 500 µl/h. As illustrated in the graph in FIG. 10, it can be seen that the device for measuring a flow velocity according to the present invention may have the performance corresponding to the performance of the device for measuring a flow velocity in the related art.

As described above, according to the present invention, the panel through which the sample passes may be replaced and used in accordance with a measuring range of a fluid flow velocity intended to be measured by a user, such that the device may be used universally without limiting the measurable range of the flow velocity.

It is apparent that the scope of the present invention is not limited to the exemplary embodiment described above and defined by the appended claims, and the exemplary embodiment may be variously modified and altered by those skilled in the art without departing from the scope defined by the appended claims.

INDUSTRIAL APPLICABILITY

The device for measuring a microfluid flow velocity according to the present invention has the industrial applicability because the device has a simple structure, the device is easy to manufacture and requires lower costs than a fluid device for measuring a flow velocity in the related art, and the device is excellent in economic feasibility and marketability.

In addition, since the panel including the microfluid channel through which a sample passes may be replaced and used, the present invention is a very useful invention that may be used universally without limiting the range of the flow velocity.

The invention claimed is:

1. A device for measuring a microfluid flow velocity, the device comprising:
a first panel comprising a flow velocity measurement structure configured to measure a flow velocity of a fluid;
a second panel configured to be separated from the first panel and comprising a microfluid channel through which a sample passes, a vacuum groove being formed in a lower surface of the second panel, and a vacuum suction portion being formed in a lateral surface of the first panel or the second panel to communicate with the vacuum groove; and
an ultra-thin film detachably placed, without being coated onto the first panel or the second panel, in a portion between the vacuum groove and the vacuum suction portion where the first panel and the second panel adjoin each other, the ultra-thin film being configured to separate the first panel and the second panel so that the sample passing through the microfluid channel does not come into direct contact with the flow velocity measurement structure,
wherein the first panel comprising the flow velocity measurement structure is usable multiple times repeatedly, and
wherein a material of the ultra-thin film comprises one or more materials selected from polydimethyl siloxane (PDMS) and polyimide (PI).

2. The device of claim 1, wherein the flow velocity measurement structure comprises:
a heater configured to apply heat to the sample passing through the microfluid channel; and
two temperature measuring electrodes installed at front and rear sides of the heater to measure a resistance difference in accordance with a change in temperature of the sample when the temperature of the sample is increased by the heat generated by the heater.

3. The device of claim 1, further comprising:
a vacuum attachment means configured to apply a vacuum to hold the first panel and the second panel by the vacuum.

4. The device of claim 3, wherein the vacuum attachment means comprises:
a vacuum suction portion configured to communicate with the vacuum groove to apply the vacuum and hold, by the vacuum, the first panel and the second panel so that an air layer between the first panel and the second panel is completely removed.

5. The device of claim 4, wherein the vacuum groove is shaped and positioned to surround the microfluid channel.

6. The device of claim 1, wherein the microfluid channel comprises:
a fluid injection port configured to inject the sample;
a fluid channel through which the sample introduced into the fluid injection port flows; and
a fluid discharge port from which the sample flowing through the fluid channel is discharged.

7. The device of claim 1, wherein the first panel and the second panel are separable, and the second panel comprising the microfluid channel through which the sample passes is replaced and used in accordance with a measuring range of a fluid flow velocity intended to be measured by a user, such that the first panel is usable universally without limiting a measurable range of the flow velocity.

8. The device of claim 1, wherein the material of the ultra-thin film comprises polydimethyl siloxane (PDMS).

9. The device of claim 1, wherein the material of the ultra-thin film comprises polyimide (PI).

10. The device of claim 1, wherein the material of the ultra-thin film comprises polydimethyl siloxane (PDMS) and polyimide (PI).

\* \* \* \* \*